United States Patent [19]

Kronick et al.

[11] 4,192,996

[45] Mar. 11, 1980

[54] MEASUREMENT OF OXYGEN BY DIFFERENTIAL ABSORPTION OF UV RADIATION

[75] Inventors: Melvyn N. Kronick; Charles E. Bryson, III; John A. Bridgham, all of Palo Alto; Sam H. Eletr, Berkeley, all of Calif.

[73] Assignee: Hewlett-Packard Company, Palo Alto, Calif.

[21] Appl. No.: 923,844

[22] Filed: Jul. 12, 1978

[51] Int. Cl.$^2$ .............................................. G01J 1/42
[52] U.S. Cl. .................................................... 250/373
[58] Field of Search ................ 250/373, 343, 344, 345

[56] References Cited

U.S. PATENT DOCUMENTS

| 3,869,613 | 3/1975 | Link et al. ............................ 250/343 |
| 4,096,388 | 6/1978 | Wong ................................... 250/373 |

Primary Examiner—Davis L. Willis
Attorney, Agent, or Firm—Ronald E. Grubman

[57] ABSTRACT

A device is provided for measuring the concentration of oxygen in a sample utilizing the differential absorption by oxygen ($O_2$) of two closely spaced ultraviolet (UV) radiation lines. The two UV lines are preferably isotope-shifted Hg lines in the vicinity of the Hg atomic transistion line at 1849.5A.

23 Claims, 10 Drawing Figures

MEASUREMENT OF OXYGEN BY DIFFERENTIAL ABSORPTION OF UV RADIATION

BACKGROUND OF THE INVENTION

The measurement of oxygen concentration in the presence of other gases is a problem of current interest, particularly in the medical field. The method of oxygen measurement most commonly used in the prior art is a "Clark" electrode cell such as that described in L. C. Clark, "Monitor and Control of Blood and Tissue $O_2$ Tension", Trans. Am. Soc. Artif. Int. Organs 2 41–46 (1956). These cells must be recalibrated often, and their use involves the repeated handling of filling solutions and delicate membranes. Other methods which have been explored for the measurement of oxygen include mass spectrometers and gas chromatographs, paramagnetic measuring techniques, solid state electrochemical devices, fluorescent quenching, and colorimetric methods. None of these methods has proven completely acceptable for oxygen measurement, particularly, in medical applications.

In U.S. patent application Ser. No. 805,551 filed by Jacob Y. Wong on June 10, 1977, entitled Measuring Gaseous Oxygen with UV Absorption (assigned to the present assignee), issued on June 20, 1978, as U.S. Pat. No. 4,096,388 there is described a system in which the spectral emission from a UV source is broadened to include different wavelengths which are either strongly or weakly absorbed by $O_2$ but are about equally absorbed by other gases. An etalon filter selectively passes the wavelengths through an oxygen containing sample, whence the difference in absorption of the two wavelengths provides an indication of the amount of $O_2$ in the sample. A device using this scheme requires an elaborate Fabry-Perot etalon filter for its operation, which is undesirable in certain applications.

SUMMARY OF THE INVENTION

In accordance with the illustrated preferred embodiments, the present invention provides a gas analyzer which utilizes the differential absorption by $O_2$ of two closely spaced ultraviolet radiation lines to measure oxygen concentration. In preferred embodiments, the two radiation lines are isotope shifted Hg (mercury) lines in the vicinity of the Hg atomic transition line at 1849.5 Å, which lies near a peak of the $O_2$ absorption spectrum at 1849.4 Å. These lines may be provided by an Hg emission lamp containing a mixture of Hg isotopes whose output is directed through a pair of filter cells, one of which contains an Hg isotope with a characteristic absorption slightly above 1849.5 Å, and the other containing an Hg isotope which absorbs slightly below 1849.5 Å. The spectrum of the Hg emission having passed through one of these filters will be shifted to one side or the other of the central 1849.5 Å wavelength. In alternate embodiments, separate sources may be employed, each containing a pure Hg isotope which emits in the vicinity of 1849.5 Å.

DETAILED DESCRIPTION OF THE INVENTION

Figure 1:
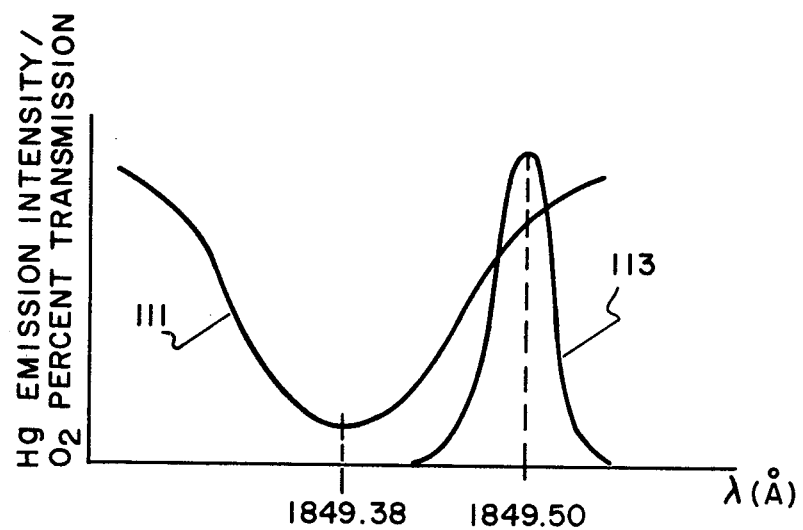
FIG. 1 shows the transmission spectrum for $O_2$ superimposed on the emission spectrum of the mercury atomic emission line at 1849.5 Å.
Figure 2:
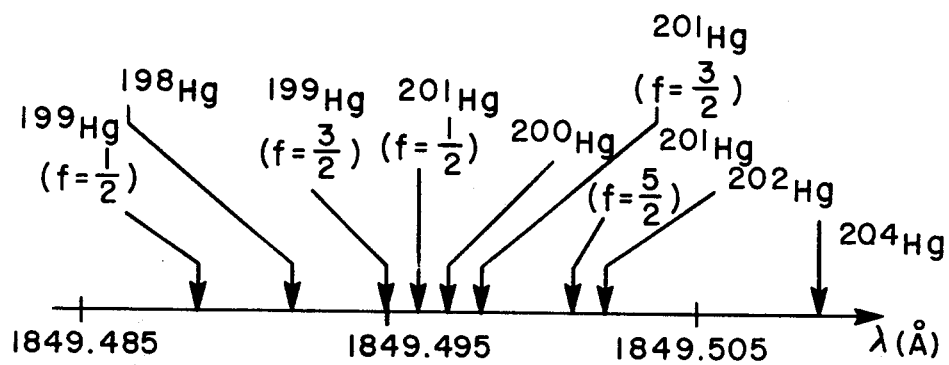
In FIG. 2 the relative positions of the isotopic lines which contribute to the mercury 1849.5 Å emission line are shown.

In FIG. 1 a curve labeled 111 schematically illustrates a transmission spectrum for $O_2$ having a transmission minimum (absorption maximum) at 1849.38 Å, and a half-width of about 0.1 Å. A second curve labelled 113 represents the atomic emission line of Hg which is centered at 1849.50 Å (which will hereinafter be designated as "$\lambda_{cg}$", the center-of-gravity of the Hg emission spectra). This Hg emission line is a superposition of emission (or absorption) lines generated by each of the Hg isotopes which are present in the lamp. In a preferred embodiment, the isotope mixture is that occurring in a natural sample of Hg. It is also possible to utilize a "synthetic" isotope mix which permits more precise control of spectral content. In FIG. 2, the relative positions of the naturally occurring isotope lines are indicated by arrows labeling the isotopic state and hyperfine state where applicable.

Figure 3A:
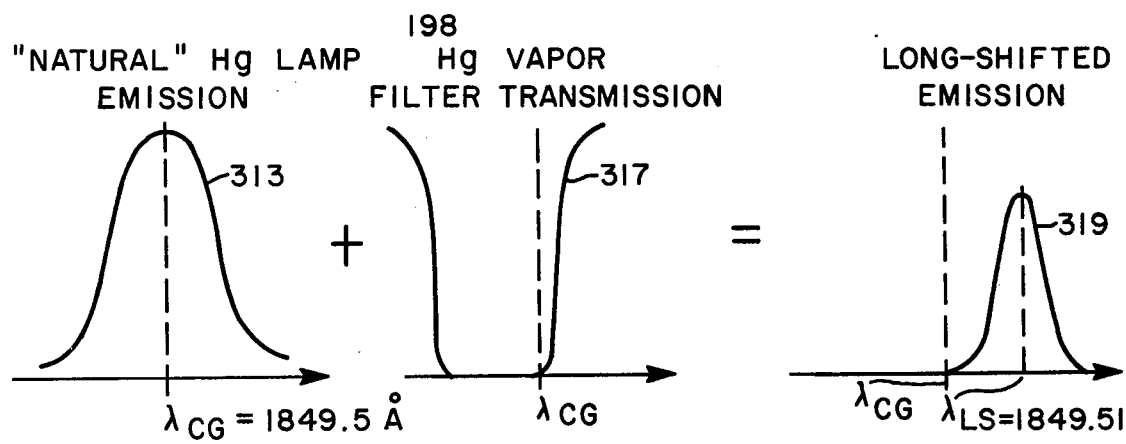
FIGS. 3A and 3B show long-shifted and short-shifted emission lines which are obtained by passing the natural mercury line through selected mercury isotopic filters.
Figure 3B:
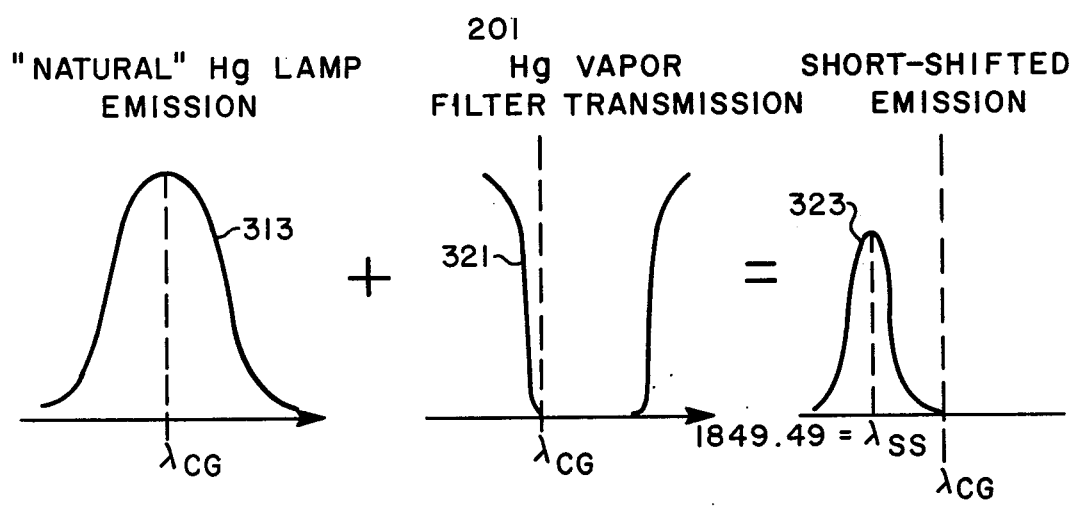

By passing the radiation emitted by an Hg lamp through a cell containing an isotope which absorbs at a wavelength below $\lambda_{cg}$ a spectrum can be obtained whose center-of-gravity will be displaced to a wavelength longer than $\lambda_{cg}$. This is illustrated in FIG. 3A for the particular case in which the filter cell contains the isotope $^{198}$Hg. In this case incident radiation 313 is passed through the filter cell having an absorption curve 317 to produce an emergent radiation spectrum 319 having a central wavelength $\lambda_{LS} \approx 1849.51$ Å, which is "long-shifted" relative to $\lambda_{cg}$. In FIG. 3B, on the other hand, a natural mercury emission spectrum 313 is passed through a filter containing $^{204}$Hg vapor having an absorption spectrum 321 to produce a resultant "short-shifted" emission spectrum 323 whose central wavelength is $\lambda_{SS} \approx 1849.49$ Å.

Figure 4:
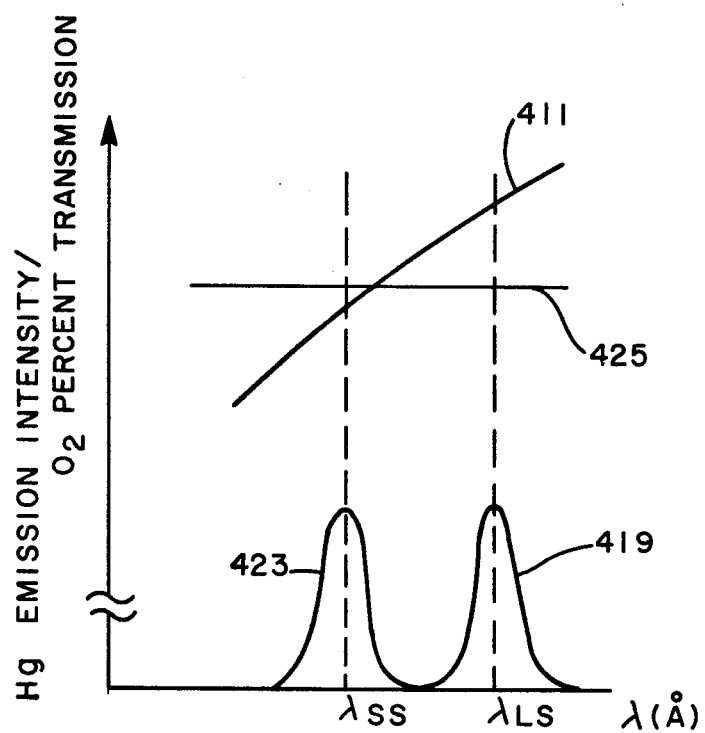
FIG. 4 shows the long-shifted and short-shifted mercury emission spectra superimposed on a portion of the $O_2$ transmission line.

FIG. 4 shows the higher wavelength edge of $O_2$ transmission curve 411 on a scale expanded from the scale of FIG. 1. Also shown are the long-shifted and short-shifted Hg emission curves 419 and 423, respectively. Because of the steepness of the $O_2$ transmission curve 411, there will be an appreciable difference between the transmission of the long-shifted and short-shifted mercury emissions when these are passed through a sample containing $O_2$. However, other UV absorbers such as H$_2$O will display an absorption curve which is essentially flat over the small wavelength region encompassing $\lambda_{SS}$ and $\lambda_{LS}$ ($\Delta L \approx 0.02$ Å). Such a curve is schematically illustrated in FIG. 4 by the line labelled 425. Thus, in a sample containing O$_2$ and other broadband UV absorbers, the other absorbers will absorb the long-shifted radiation 419 and short-shifted radiation 423 about equally, while the O$_2$ will absorb these differentially. A measurement of the difference in the percent absorption of these two lines will therefore give an indication of the amount of O$_2$ which is present in the sample.

It should be noted that U.S. Pat. No. 3,869,613 issued Mar. 4, 1975 to W. T. Link, et al. discloses a device for detecting a specific gas using an infra-red beam which is alternately passed through different filter cells containing different isotopes of the specific gas to be detected. The beam emerging from each filter cell will have had removed the wavelength corresponding to the isotope in that cell. In the patent the isotopes are selected as those which occur in different proportions in the specific gas to be detected. Thus, the two beams will be absorbed differently by the sample (containing different proportions of the isotopes), but will be absorbed about equally by other absorbers.

For the detection of O$_2$ this technique would entail the use of a broadband UV source (in place of an infrared source) generating a beam to be passed through filter cells containing different isotopes of O$_2$. Such a procedure does not appear to be useful for the detection of O$_2$, because any band of UV radiation sufficiently narrow to have essentially constant absorption of interfering gases over that band will be too narrow to allow wavelength shifting by oxygen isotopes.

The present O$_2$ detection device differs from that disclosed in the above-referenced patent in various respects: No broadband UV source is used; instead a narrow line source from an atomic transition of an element (e.g. mercury) is employed. Further, no isotopes of the specific gas to be detected (i.e. O$_2$) are used, rather; the present invention employs isotopes of only the radiation source element.

Figure 5:
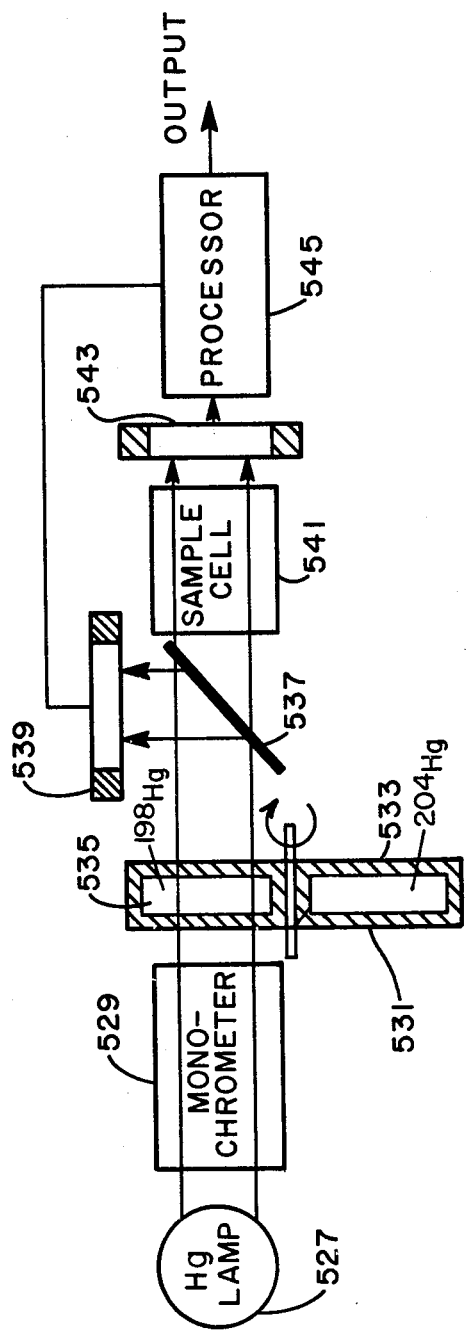
FIG. 5 schematically illustrates an $O_2$ detection system utilizing the long-shifted and short-shifted mercury emission spectra.

FIG. 5 shows a simple system for implementing the oxygen detection scheme discussed above. A mercury vapor lamp 527 emits a spectrum characteristic of the atomic transistions of Hg, including a radiation line centered about 1849.5 Å. This particular transition line includes radiation from the various isotopes shown in FIG. 2. Radiation from mercury lamp 527 is passed through a monochromator 529 which filters out all of the mercury emission except a small bandwidth centered on the 1849.5 Å line. For example, an Acton Research Corporation 185-N filter (Acton,Ma) may be used which has a half-width of about 275 Å. The mercury radiation which has passed through monochromator 529 is then passed through a filter wheel 531 which includes filter cells 533 and 535 each containing a single isotope of mercury whose absorption peak lies on one side or the other 1849.5 Å emission line. The Hg isotope in the cell preferably consists of a small amount of liquid Hg in equilibrium with its vapor. For example, one cell may contain $^{198}$Hg and the other cell $^{204}$Hg. Cells 533 and 535 should provide a pathlength greater than about two millimeters to provide adequate absorption. Filter wheel 531 is rotated to present alternately one or the other of cells 533 and 535 in the path of the emission from lamp 527. Thus, in accordance with the discussion above, radiation having passed through one cell or the other will display a short-shifted or long-shifted emission spectrum. The radiation emergent from filter wheel 531 is incident upon a beamsplitter 537 such as a quartz plate with a thin aluminum coating so that a portion of the radiation is directed to a "reference" detector 539 while another portion of the radiation is directed through a sample cell 541 to a "sample" detector 543. In order to prevent the occurrence of spurious signals arising from ambient O$_2$ which may be present in the vicinity of the filter wheel, sample cell etc., the optical path length from beamsplitter 537 to reference detector 539 should be equal to the optical path length from beamsplitter 537 to sample detector 543, less the length of sample cell 541. Alternately, the system can be hermetically sealed to prevent any spurious O$_2$ from entering the system.

Sample cell 541 contains a gas to be analyzed including an amount of oxygen to be determined by the measurement, so that sample detector 543 provides an indication of the intensity of the long-shifted and short-shifted radiation transmitted through the oxygen-containing sample. Reference detector 539 on the other hand provides an indication of the intensity of the long-shifted and short-shifted emission spectra which has not been subject to absorption by the sample. Use of a beamsplitter and reference detector therefore renders the detection scheme insensitive to sources of long-term drift, such as temperature variations, power variations etc. If these are insignificant in a given system, the reference detector can be omitted.

In accordance with the discussion above, the difference in the amounts of the long-shifted and short-shifted emission spectra detected by detectors 539 and 543 therefore gives an indication of the amount of oxygen present in sample cell 541.

To make the detection scheme discussed above more precise consider the following definitions:

$I_{LS,R}$ = Signal amplitude at reference detector due to light which passed through the $^{198}$Hg cell.

$I_{SS,R}$ = Signal amplitude at reference detector due to light which passed through the $^{204}$Hg cell.

$D_R$ = Signal at reference detector when no light falls on it.

In terms of these quantities the following amplitudes $I_{1,R}$ through $I_{4,R}$ can be measured at the reference detector 539;

$$I_{1,R} = I_{LS,R} + D_R \quad (1)$$
$$I_{2,R} = D_R \quad (2)$$
$$I_{3,R} = I_{SS,R} + D_R \quad (3)$$
$$I_{4,R} = D_R \quad (4)$$

Consider now the radiation passing through sample cell 541 containing a certain partial pressure of oxygen defined as "pO$_2$". This amount of O$_2$ will produce an attenuation of the short-shifted and long-shifted spectra by a factor of $\exp(-K_{SS}pO_2)$ and $\exp(-K_{LS}pO_2)$ respectively, where $K_{SS}$ and $K_{LS}$ are attenuation coefficients characteristic of the two spectra. Additional attenuation due to absorption by water, scattering, deflections, etc. will also occur, and is accounted for by a factor of $\exp(-c)$, where c is the same constant for both the short-shifted and long-shifted radiation (see the discussion of FIG. 4). Thus, analagously to the reference amplitudes $I_{1,R}$-$I_{4,R}$, the following amplitudes can be measured at sample detector 543:

$$I_{1,S} = I_{LS,S}(e^{-K_{LS}pO_2}e^{-c}) + D_S \quad (5)$$

-continued $$I_{2,S} = D_S \qquad (6)$$
$$I_{3,S} = I_{SS,S}(e^{-K_{SS}pO_2}e^{-c}) + D_S \qquad (7)$$
$$I_{4,S} = D_S \qquad (8)$$

A ratio R can now be formed and manipulated, preferably by means of an associated digital electronics processor 545, as follows:

$$R = \left(\frac{I_{1,S} - I_{2,S}}{I_{3,S} - I_{4,S}}\right) \bigg/ \left(\frac{I_{1,R} - I_{2,R}}{I_{3,R} - I_{4,R}}\right) \qquad (9)$$

$$R = \left(\frac{I_{LS,S} e^{-K_{LS}pO_2} e^{-c}}{I_{SS,S} e^{-K_{SS}pO_2} e^{-c}}\right) \bigg/ \left(\frac{I_{LS,R}}{I_{SS,R}}\right) \qquad (10)$$

Since beamsplitter 537 does not alter the ratio of long-shifted to short-shifted light incident upon the reference detector 539 and the sample cell 541, $$\frac{I_{LS,S}}{I_{SS,S}} = \frac{I_{LS,R}}{I_{SS,R}} \qquad (11)$$

Thus, $$R = e^{-(K_{LS} - K_{SS})pO_2}, \qquad (12)$$

from which the partial pressure of oxygen is given by $$pO_2 = \frac{\ln(R)}{K_{SS} - K_{LS}} \qquad (13)$$

Figure 6:
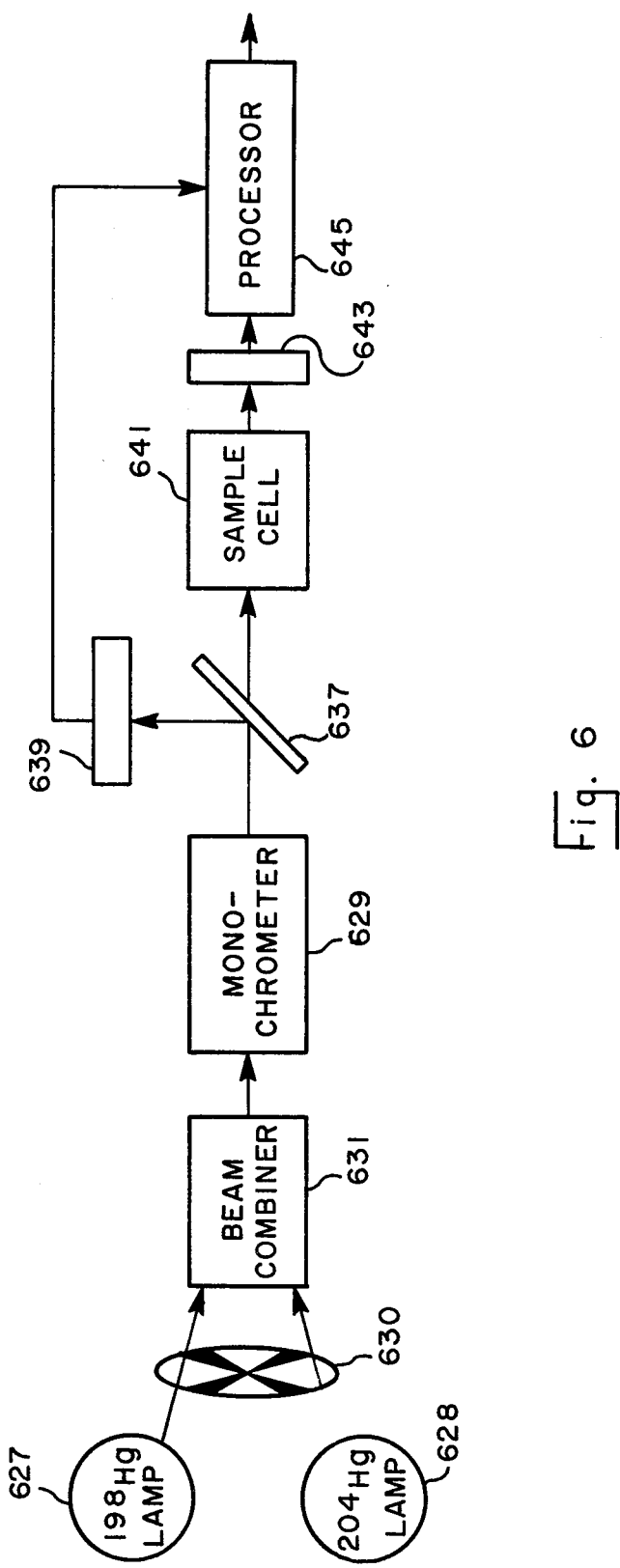
FIG. 6 illustrates an oxygen detection system in which separate mercury isotopic lamps supply the different spectra used for the oxygen detection.

In an alternate embodiment the oxygen absorption curve may be differentially detected using two separate isotopic lines of the mercury ultraviolet emission line close to 1849.5 Å. In this embodiment, shown in FIG. 6, two separate sources are provided, each containing a pure mercury isotope. For example, FIG. 6 shows a lamp 627 containing substantially pure $^{204}$Hg. Thus, each of the lamps will display an emission spectrum near the 1849.5 Å Hg line which is characteristic of the pure isotope contained in that lamp. These spectra are switched into a beam combining element 631 similar to beamsplitter 537 in FIG. 5. The switching may be accomplished mechanically, for example by using a rotating wheel 630 as shown. Alternatively, electrical beam switching could be accomplished by electrically modulating the intensities of lamps 627 and 628. The combined beam is directed through a monochromator 629 such as the monochromator 529 in FIG. 5 having a passband centered on 1849.5 Å. The remaining elements of the system including a beamsplitter 637, sample cell 641, reference detector 639, and sample detector 643 are the same as the equivalent elements in FIG. 5. Operation of the device of FIG. 6 is governed by the same equations as described above with respect to the device of FIG. 5. However, since the two slightly different Hg spectra are here provided by the two different pure isotope lamps 627 and 628, the amount of oxygen present in the sample cell will ultimately be determined by the equation $$pO_2 = \frac{\ln(R)}{K_{198} - K_{204}}, \qquad (14)$$

where $K_{198}$ and $K_{204}$ represent the oxygen absorption coefficients for the $^{198}$Hg and $^{204}$Hg isotope emission lines, respectively.

In an alternate embodiment each lamp can be a "natural" Hg lamp having an associated isotope filter, in which case the above discussion yields an expression similar to Equation 14 where $K_{198}$ and $K_{204}$ are replaced by $K_{SS}$ and $K_{LS}$, as earlier defined.

Figure 7:
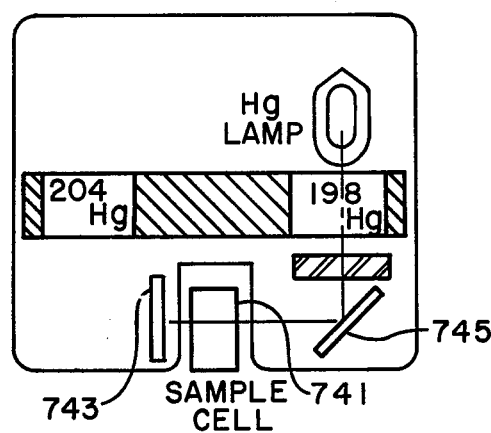
FIG. 7 shows a system in which a separate beamsplitter is not required.

In FIG. 7 there is shown an embodiment in which a sample detector 743 and a reference detector 745 are silicon photodetectors, such as a model UV100B manufactured by EG&G Company in Salem, Massachusetts. The silicon surface of reference detector 745 is highly reflective to the UV radiation utilized in the present $O_2$ detection scheme. It is thus possible to use the surface of reference detector 745 to deflect a portion of the optical beam through sample cell 741, while absorbing another portion of the beam as a reference signal. In this embodiment the requirement for a separate beamsplitter is eliminated.

Figure 8:
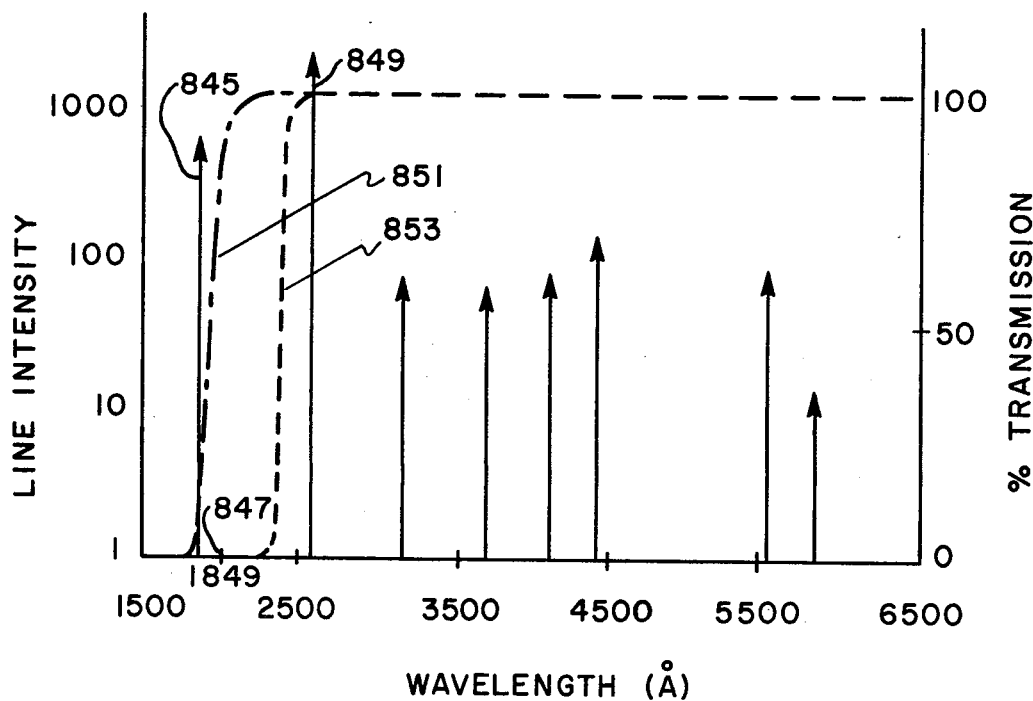
FIG. 8 shows the transmission curves for water and Vycor ® superimposed on the mercury atomic emission lines.

To facilitate implementation of the oxygen detector in a compact and inexpensive package some preferred embodiments of the invention may utilize techniques other than or in addition to a monochromator for eliminating the mercury atomic emission lines other than the 1849 Å line. This may be accomplished pursuant to FIG. 8 which shows the Hg atomic emission lines in the ultraviolet. The line labeled 845 is the 1849 Å line which overlaps the oxygen absorption spectra. A low intensity line labelled 847 occurs at a wavelength of 1942 Å and a high intensity line labeled 849 occurs at a wavelength of 2537 Å. FIG. 8 also shows a transmission curve 851 for a nominal 3 mm thickness of $H_2O$ and another transmission curve 853 for a nominal 3 mm thickness of Vycor ®, a 96% pure quartz material which does not transmit short wavelength ultraviolet light. From FIG. 8 it can be seen that if radiation from a mercury lamp is passed through a cell containing $H_2O$, the 1849 Å line will be filtered out of the emission spectra. Similarly, if the mercury radiation is passed through a Vycor ® element all emission lines having wavelengths shorter than 2500 Å (including the 1849 Å line) will be filtered out.

The relationships among the mercury emission lines and the transmission characteristics of water or Vycor ® illustrated in FIG. 8 may be exploited in a device according to the present invention by observing that $$I_{TOTAL} = I_{1849} + I_{OTHER} \qquad (15)$$

where $I_{TOTAL}$ is the total Hg intensity of the Hg atomic emission spectrum, $I_{1849}$ is the intensity of the atomic emission at 1849 Å and $I_{OTHER}$ is the combined intensities of all other Hg emission lines at wavelengths longer than 1849 Å. This relationship can also be expressed as $$I_{1849} = (I_{1849} + I_{OTHER}) - I_{OTHER}. \qquad (16)$$

Thus, $I_{1849}$ may be inferred by measuring the total mercury emission and also measuring the mercury emission having the 1849 Å line eliminated. The difference of these will be $I_{1849}$.

If the radiation is passed through the $^{198}$Hg and $^{204}$Hg filters as discussed above in connection with FIG. 3, an emergent radiation is governed by the equivalent relationships for long-shifted and short-shifted emissions:

$$I_{1849,LS} = (I_{1849,LS} + I_{OTHER}) - I_{OTHER}, \quad (17)$$
$$I_{1849,SS} = (I_{1849,SS} + I_{OTHER}) - I_{OTHER} \quad (18)$$

Figure 9:
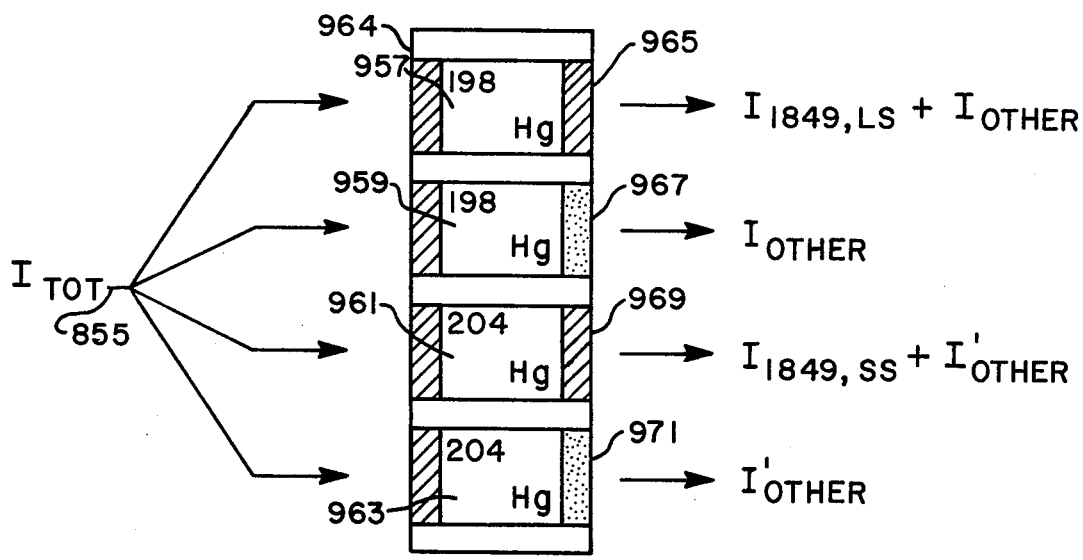
FIG. 9 shows how a number of filter cells could be used to produce selected mercury lines for an oxygen detection device.

FIG. 9 shows a schematic representation of a filter system for the determination of $I_{1849,LS}$ and $I_{1849,SS}$ according to the equations above.

A beam of radiation 955 is emitted from a mercury source (not shown). Radiation beam 955 is incident upon four cells 957, 959, 961 and 963, two of which contain $^{198}$Hg (cells 957 and 959), and two of which contain $^{204}$Hg (cells 961 and 963). The entry and exit windows 964 and 965 of cell 957 are of a material which transmits all of the wavelengths in the mercury ultraviolet emission spectrum; e.g. Suprasil ® quartz windows are suitable. Thus, the radiation emergent from cell 957 will contain all mercury emission lines including specifically the 1849 Å line. However, because of the presence of the $^{198}$Hg isotope in cell 957 the 1849 Å line will be long-shifted, as was discussed above in connection with FIG. 3.

The radiation emergent from cell 957 will therefore have an intensity of $I_{1849,LS} + I_{OTHER}$. Cell 959 includes at least one window, e.g. an exit window 967, of a material such as Vycor ® which effectively blocks transmission of the mercury 1849 Å line. Thus, the radiation emitted from cell 959 will have an intensity $I_{OTHER}$ (In an alternate embodiment, H$_2$O could be incorporated into the cell in lieu of the Vycor ® window, which would also yield a spectrum in which the 1849 Å line would be absent).

In a similar manner radiation passing through cell 961 containing $^{204}$Hg and Suprasil ® windows 869 will emerge having an intensity of $I_{1849,SS} + I'_{OTHER}$, while radiation passing through cell 963 having a Vycor ® window 971 will emerge with an intensity $I'_{OTHER}$.

To make the oxygen measurement each of the beams emerging from the filter cells in FIG. 9 is directed to the sample and reference detectors as described above in connection with FIG. 5. For example, the various cells of FIG. 9 may be configured in a rotating filter wheel such as the one illustrated in FIG. 5. The intensities measured at the sample and reference detectors are electronically stored, e.g. in a digital calculating apparatus and are combined according to equations 17 and 18. Note that if extreme accuracy is required, it may be necessary to account for small differences in transmissivity between e.g. cells 957 and 959, so that $I_{OTHER}$ exactly cancels in Equation 16. This can be accomplished e.g. by calculating a normalizing coefficient based on a comparison of the intensities of radiation passing through the two cells when $I_{1849}$ is blocked. The normalized combined intensity values are then inserted into equation 13 to indicate the partial pressure of O$_2$ in the sample cell.

We claim:

1. A device for measuring the concentration of O$_2$ in a sample comprising:
   source means for providing a primary UV radiation beam from an atomic transition of an element at a nominal wavelength in a spectral region where the transmissivity of oxygen is rapidly varying, said beam including at least one transition line of a first isotope of said element at a wavelength higher than said nominal wavelength, and at least one transition line of a second isotope of said element at a wavelength lower than said nominal wavelength;
   shifting means for producing from said primary radiation beam a short-shifted radiation beam having an intensity distribution weighted toward said isotope line of wavelength lower than said nominal wavelength, and producing a long-shifted radiation beam having an intensity distribution weighted toward said isotope line of wavelength higher than said nominal wavelength;
   beam directing means for directing said long-shifted and short-shifted radiation beams through said sample;
   detection means for detecting the intensities of said long-shifted and short-shifted radiation beams having been transmitted through said sample; and
   processing means for calculating from said intensities an indication of the concentration of oxygen in said sample.

2. A device as in claim 1 wherein:
   said shifting means comprises a first cell containing said first isotope and a second cell containing said second isotope, said primary beam being directed through said first cell to produce said short-shifted beam and being directed through said second cell to produce said long-shifted beam.

3. A device as in claim 2 wherein:
   said shifting means further comprises filter means for altering said short-shifted and long-shifted beams by eliminating the emission line at said nominal wavelength during a portion of said measurement; and
   said processing means utilizes intensities derived from said altered short-shifted and long-shifted beams having passed through said sample as a correction in the calculation of the concentration of oxygen in said sample.

4. A device as in claim 3 further comprising:
   reference detection means for detecting the intensities of portions of each of said short-shifted and long-shifted beams which have not passed through said sample, these intensities being utilized by said processing means in calculating said indication of the concentration of oxygen in the sample.

5. A device as in claim 4 wherein:
   said primary UV radiation beam is from an atomic transition of the element mercury.

6. A device as in claim 5 wherein:
   said atomic transition of mercury produces an emission line at about 1849.5 Å.

7. A device as in claim 4 wherein:
   said reference detection means comprises a silicon photodetector having a surface which is highly reflective to UV radiation in the vicinity of said nominal wavelength, said reference detection means being spatially positioned to direct reflected portions of said short-shifted and long-shifted radiation beams through said sample while absorbing other portions of said beams and detecting the intensities thereof.

8. A device as in claim 7 wherein:
   said primary UV radiation beam is from an atomic transition of the element mercury.

9. A device as in claim 8 wherein:
   said atomic transition of mercury produces an emission line at about 1849.5 Å.

10. A device as in claim 2 further comprising:
    monochromator means in the path of said radiation between said source and said sample, for eliminating from said primary UV radiation beam all emission lines except those in a small bandwidth centered on said nominal wavelength.

11. A device as in claim 10 further comprising:
reference detection means for detecting the intensities of portions of each of said short-shifted and long-shifted beams which have not passed through said sample, these intensities being utilized by said processing means in calculating said indication of the concentration of oxygen in the sample.

12. A device as in claim 11 wherein:
said primary UV radiation beam is from an atomic transition of the element mercury.

13. A device as in claim 12 wherein:
said atomic transition of mercury produces an emission line at about 1849.5 Å.

14. A device as in claim 2 wherein:
said primary UV radiation beam is from an atomic transition of the element mercury.

15. A device as in claim 14 wherein:
said atomic transition of mercury produces an emission line at about 1849.5 Å.

16. A device for measuring the concentration of oxygen in a sample comprising:
source means for providing a first UV radiation beam from an atomic transition line of a first isotope of an element, and a second UV radiation beam from an atomic transition line of a second isotope of said element, said first and second transition lines having wavelengths near a nominal wavelength in a spectral region where the transmissivity of oxygen is rapidly varying;
directing means for directing said first and second radiation beams through the sample;
detection means for detecting the intensities of said first and second radiation beams having been transmitted through said sample; and
processing means for calculating from said intensities an indication of the concentration of oxygen in the sample.

17. A device as in claim 16 wherein said source means comprises:
a first cell containing said first isotope of said element, which is excited to provide said first radiation line; and
a second cell containing said second isotope of said element, which is excited to provide said second radiation line.

18. A device as in claim 17 wherein said source means further comprises:
beam combining means for combining said first and second radiation beams into a combined beam; and
switching means for alternatingly directing said first and second radiation beams from said first and second cells into said beam combining means.

19. A device as in claim 18 further comprising:
monochromator means in the path of said combined beam for eliminating from said combined beam all emission lines except those in a small bandwidth centered on said nominal wavelength.

20. A device as in claim 19 wherein:
said first and second isotopes are isotopes of the element mercury.

21. A device as in claim 20 wherein:
said atomic transition of mercury produces an emission line at about 1849.5 Å.

22. A device as in claim 16 wherein:
said first and second isotopes are isotopes of the element mercury.

23. A device as in claim 22 wherein:
said atomic transition of mercury produces an emission line at about 1849.5 Å.

* * * * *

UNITED STATES PATENT AND TRADEMARK OFFICE
CERTIFICATE OF CORRECTION

PATENT NO. : 4,192,996  Page 1 of 2
DATED : March 11, 1980
INVENTOR(S) : Melvyn N. Kronick, et al It is certified that error appears in the above-identified patent and that said Letters Patent are hereby corrected as shown below:

In the Abstract, on the 6th line, delete "1849.5A" and insert --$1849.5\overset{\circ}{A}$--.

Column 1, line 14, delete "2" and insert --$\underline{2}$--.

Column 4, line 68, delete "$(e^{-KLSpO_2}e^{-c})$" and insert --$(e^{-K_{LS}pO_2}e^{-c})$--.

Column 5, line 3, delete "$(e^{-KSSpO_2}e^{-c})$" and insert --$(e^{-K_{SS}pO_2}e^{-c})$--.

Column 5, line 14, delete "$I_{LS,S}e^{-KLSpO_2}e^{-c}$" and insert --$I_{LS,S}e^{-K_{LS}pO_2}e^{-c}$--.

Column 5, line 15, delete "$I_{SS,S}e^{-KSSpO_2}e^{-c}$" and insert --$I_{SS,S}e^{-K_{SS}pO_2}e^{-c}$--.

UNITED STATES PATENT AND TRADEMARK OFFICE
CERTIFICATE OF CORRECTION

PATENT NO. : 4,192,996
DATED : March 11, 1980
INVENTOR(S) : Melvyn N. Kronick, et al It is certified that error appears in the above-identified patent and that said Letters Patent are hereby corrected as shown below:

Column 5, line 12, delete "(KLS - KSS) and insert --$(K_{LS} - K_{SS})$--.

Signed and Sealed this

Eighth Day of July 1980

[SEAL]

Attest:

SIDNEY A. DIAMOND

Attesting Officer

Commissioner of Patents and Trademarks